United States Patent [19]

Shalitin

[11] Patent Number: 4,767,714

[45] Date of Patent: Aug. 30, 1988

[54] METHOD FOR THE PREPARATION OF YEAST CHROMATIN FOR ISOLATION OF P20 POLYPEPTIDE

[75] Inventor: Channa Shalitin, Haifa, Israel

[73] Assignee: Technion Research & Development Foundation Ltd., Haifa, Israel

[21] Appl. No.: 753,963

[22] Filed: Jul. 11, 1985

[30] Foreign Application Priority Data

Jul. 19, 1984 [IL] Israel ............................. 72452

[51] Int. Cl.$^4$ .............................................. C07K 3/12
[52] U.S. Cl. ...................................... 435/272; 435/68; 530/824
[58] Field of Search ............... 530/824; 435/68, 272

[56] References Cited

U.S. PATENT DOCUMENTS 3,867,255  2/1975  Newell et al. ................. 530/824
3,960,659  6/1976  Fazakerley .................... 530/824
3,996,104  12/1976 Gunilla et al. ................. 530/824

OTHER PUBLICATIONS

Gulloev et al–Chem. Abst. vol. 94 (1981), p. 61282f.

Primary Examiner—Sam Rosen
Attorney, Agent, or Firm—Browdy and Neimark

[57] ABSTRACT

A method for the preparation of pure yeast chromatin for isolation of p20 polypeptide includes breaking yeast cells in a buffer solution and separating the released chromatin. The chromatin is purified through sucrose, solubilized by an enzymatic digestion and the supernatant solution is loaded on a linear sucrose gradient 5-30% in a buffer solution. The p20 polypeptide is extracted from the sucrose gradient fraction by a buffer solution comprising sodium chloride at a concentration in the range of 0.15-5 M and preferably in the range of 0.35 M to 2.0 M.

14 Claims, 3 Drawing Sheets

METHOD FOR THE PREPARATION OF YEAST CHROMATIN FOR ISOLATION OF P20 POLYPEPTIDE

The present invention relates to a new method for the preparation of yeast chromatin and its use for obtaining antibodies for the detection of mammalian carcinomas. More particularly, the invention relates to a new, simple and inexpensive method for the preparation of pure yeast chromatin and its use for obtaining antibodies which are very specific in their binding properties towards mammalian ras gene products. Chromatin is known as a nucleoprotein complex composed of four major constituents:

histones, which are low molecular weight proteins;
nonhistone proteins which are distinguishable from histones;
deoxyribonucleic acid (so called DNA), and
ribonucleic acid (so called RNA).

Figure 1:
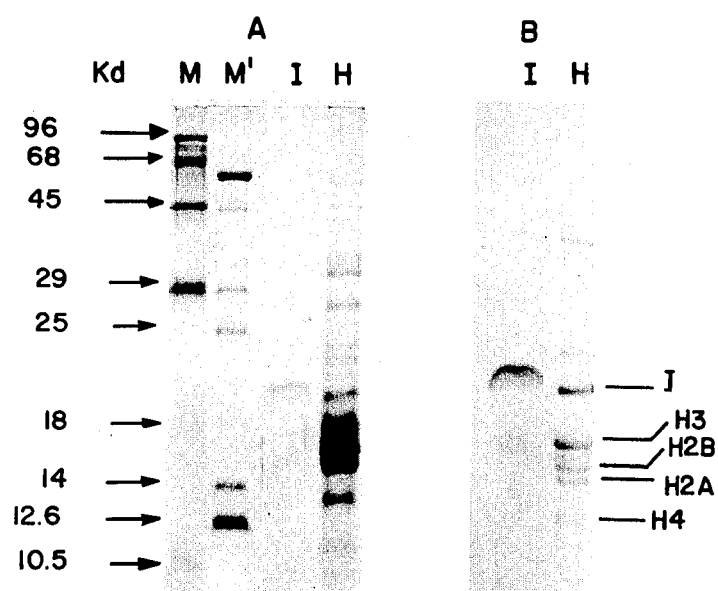

The appearance of chromatin varies with the state of the cell and the process of fixation. A number of proteins having a molecular weight of about 20,000–21,000 have been reported in connection with chromatin isolated from *Saccharomyces cerevisiae*. In a recent report, Andreas Sommer (Molec. gen. Genet. 161, 323–331, 1978), in his search for histone H1-like protein, mentioned a protein with a molecular weight of 21,000 isolated from baker's yeast (*Saccharomyces cerevisiae*). He called this protein Band I, considering it to be similar to H1 histone. As mentioned in the report, analysis by 15% polyacrylamide-sodium dodecyl sulfate gel electrophoresis has shown that Band I migrates a little slower than histone H3 (FIG. 1). In order to elucidate the basic mechanism of eukaryotic gene expression and regulation, Sommer selected *Saccharomyces cerevisiae* as an experimental model with a genetic make-up of limited complexity, as an ideal eukaryotic system. Band I was extracted from yeast chromatin by a solution of 5M sodium chloride and the released protein could be bound to Biorex 70. Elution with 550 mM sodium chloride resulted in the recovery of Band I protein. If yeast chromatin was digested by micrococcal nuclease and the digest fractionated on a sucrose gradient, the major acid extractable protein component in the top peak was found to be Band I protein. Therefore Sommer concluded that Band I protein is located in internucleosomal spaces. Furthermore, Sommer found that chromatin preparations isolated in the absence of the detergent Nonidet P40 (NP40) contained significantly reduced amounts of Band I protein. The amino acid composition of Band I (as given in Table 1) was found to be substantially similar to HMG-2 (high mobility group 2) protein, isolated from calf thymus chromatin.

In another report by F. Caron et al. (Proc. Natl. Acad. Sci. USA 76, 4265–4269, 1979) a method for extraction of a histone-like protein from yeast mitochondria was described. The method involves breaking the cells, isolating mitochondria and purifying the protein on a double-stranded calf thymus DNA-cellulose column following DNase I treatment. The protein was eluted by a solution of 2M sodium chloride and was called HM protein. According to the report by Caron et al., yeast mitochondria do not contain histones but have in abundance a 20,000 dalton DNA-binding protein which they called HM. According to the analysis of the amino acid composition (see Table 1), as given in the above report, it appears that the amino acid composition of the HM protein is substantially similar to that described by Sommer for Band I protein. However, Caron et al. considered that their HM protein is not identical to the band I protein due to the different mobility of HM protein on acid-urea polyacrylamide gels. The binding of HM protein to DNA was tested by Caron et al. using relaxed Simian virus 40 (SV40) DNA. Their reaction mixture contained a chromatin extract from Krebs ascites cells containing a nicking-closing activity. They found that the optimal conditions for the introduction of superhelical turns in relaxed SV40 DNA by HM protein are at 150 mM sodium chloride and at a HM to DNA ratio (by weight) of 0.8:1.2.

In another recent report by S. Weber and I. Isenberg (Biochemistry Vol. 19, 2236–2240, 1980), a protein called HMGa isolated from *Saccharomyces cerevisiae* is described. This protein is reported to possess a high mobility group property. It was obtained from chromatin by extraction with a solution of 0.25M hydrochloric acid. According to this report, the protein HMGa cannot be defined according to its extractability criteria. Based on its mobility in sodium dodecyl sulfate and acetic-acid urea gels, and its amino acid composition, the authors concluded that the protein Band I of Sommer is actually identical to the HMGa protein.

In a very recent report by Ulrich Certa et al. (Nucleic Acids Res. vol. 12, 7975–7985, 1984) another purification procedure of "histone H1-like" protein (20 Kd) is described. According to that procedure, the 20 Kd protein was prepared as described by Sommer from commercial bakers' yeast (*Saccharomyces cerevisiae*) using reversed phase high-performance-liquid-chromatography which included the exposure of the protein to high concentrations of acetonitrile—an unphysiological environment.

By a thorough analysis of the above mentioned proteins isolated from *Saccharomyces cerevisiae* it was found that, according to the present invention, all the above mentioned proteins have the same mobility on acetic-acid urea gels (all move a little slower than calf thymus histone H1). It was discovered that purified chromatin (free of ribosomes) from *Saccharomyces cerevisiae* (baker's yeast) can be a source of p20 polypeptide. It was further found that the p20 polypeptide thus obtained could introduce superhelical turns in relaxed pMB9 DNA (FIG. 2) as previously described by Caron et al. for HM protein isolated from yeast mitochondria. Furthermore, it was found that the p20 polypeptide is useful for the production of antibodies which possess the ability to detect ras oncogene products. Thus, according to one embodiment the invention consists of a method for the preparation of pure yeast chromatin which comprises the steps of: (a) breaking the yeast cells in a solution of a buffer and centrifugation of the slurry; (b) the precipitated pellet of chromatin is purified by centrifugation through sucrose, and washed with a buffer solution comprising 2-mercaptoethanol and phenylmethylsulfonyl fluoride; (c) the resulted precipitate from step (b) is solubilized by an enzymatic digestion; (d) loading the supernatant solution from the solubilized mass of step (c) on a linear sucrose gradient 5–30% in a buffer; and (e) extracting the p20 polypeptide from sucrose gradient fractions by a buffer solution comprising sodium chloride at a concentration in the range of 0.15M–5M. It was found that the isolated p20 polypeptide produced according to the present invention is of a high purity according to the resolution obtained by gel electrophoresis in sodium dodecyl sulfate, followed by staining with Coomassie brilliant blue R-250, as illustrated in FIG. 1A, or a silver staining procedure, as illustrated in FIG. 1B. The main band was estimated to account for more than 90% of the total material. The isolated p20 polypeptide was also pure according to electrophoresis in acetic acid-urea gel (FIG. 3). The amino acid composition of the p20 polypeptide is given in Table 1, for comparison with the proteins mentioned in the preamble of the specification. From the above Table it can be concluded that no significant differences exist in their composition, all of them being characterized by a high aspartic acid and glutamic acid content (21.8–27.0 mole%) and a lysine to arginine ratio in the range of 2.31–3.1.

The method of preparation of the p20 polypeptide, according to the present invention, is very simple to apply on a commercial scale without requiring complicated or special equipment. Furthermore, the starting raw material—baker's yeast—is abundantly available at very low prices. The term, yeast, as utilized in the present invention, encompasses any strain of Saccharomyces, Schizosaccharomyces (such as *Saccharomyces cerevisiae* and *Schizosaccharomyces pombe*) and includes partially broken cells, isolated nuclei or mitochondria.

In the first step (a) baker's yeast was washed with a solution of buffer A consisting of Tris-HCl (pH=7.5), EDTA, magnesium sulfate and sodium bisulfite, and resuspended in fresh buffer A which also contains phenylmethylsulfonyl fluoride. Cells were broken by shaking several times with glass beads, preferably coated with Sigma-cote. The decanted supernatant solution was pooled, and a new portion of phenylmethylsulfonyl fluoride added and spun. The viscous top layer of the pellet was again suspended in a solution containing, as above, buffer A+phenylmethylsulfonyl fluoride, and spun again. In step (b) the chromatin pellet was resuspended in a cold buffer containing sucrose, a detergent such as NP40, phenylmethylsulfonyl fluoride and 2-mercaptoethanol. It was found that the presence of the latter component is absolutely essential for assisting the purification of the chromatin. The concentration of the sucrose may be selected in a broad range, preferably between 0.3M to 1.7M and most preferably between 1.4M to 1.6M. The resuspended chromatin in the above mentioned buffer was spun and the resulting pellet was dispersed in the same buffer and further purified by centrifugation through a sucrose solution in a buffer comprising buffer A+phenylmethylsulfonyl fluoride and 2-mercaptoethanol. The slurry obtained was spun again at 4° C. According to a preferred embodiment, said centrifugation is carried out at least twice, the first at a lower g and the second at a higher g, which was found to assist the extent of purification. In step (c), the precipitate obtained from step (b) was solubilized by an enzymatic digestion such as DNaseI or micrococcal nuclease. After incubation, as known in the art, the suspension was centrifuged and separated.

Figure 4:
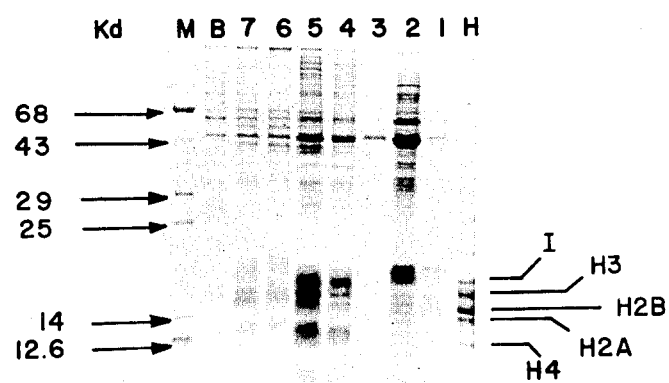

In step (d) the supernatant solution, mixed with a buffer containing phenylmethylsulfonyl fluoride, was loaded on a linear sucrose gradient 5–30% (by weight) in a buffer solution containing Tris-HCl (pH 7.5), EDTA, phenylmethylsulfonyl fluoride, sodium bisulfite and 2-mercaptoethanol. Gradients were run at 4° C. at 153,000 g. The fractions were dialyzed overnight versus acetic acid (0.1M), lyophilized and analyzed on sodium dodecyl sulfate-15% polyacrylamide gels. The results are shown in FIG. 4, illustrating a 15% polyacrylamide-sodium dodecyl sulfate gel of proteins released from yeast chromatin by micrococcal nuclease and fractionated on 5–20% linear sucrose gradients. In the figure the following terms were utilized:

M=molecular weight standards: bovine serum albumin (68 kd), ovalbumin (43 kd), carbonic anhydrase (29 kd), chymotrypsinogen (25 kd), lysozyme (14 kd), ribonuclease (12.6 kd), Lane H: yeast histones acid extracted according to the procedure of Sommer. Lanes 1–7: gradient fractions Nos. 1–7, fraction No. 1 is the top of the gradient and B is the bottom fraction.

As can be seen from FIG. 4, the p20 polypeptide splits into two bands (lane 2). The upper band of the doublet in the sodium dodecyl sulfate-polyacrylamide gels has an apparent molecular weight of 20,500. In contrast, the polypeptide isolated by acid extraction migrates as a single band (FIG. 4, lane H). Finally, in step (e) the p20 polypeptide was extracted from the sucrose gradient fractions by a sodium chloride solution mixed with a buffer Tris-HCl (pH=8), EDTA, dithioerythritol (DTE) and two protease inhibitors such as phenylmethylsulfonyl fluoride and sodium bisulfite. This is a most important step found, according to the present invention, to be absolutely necessary in order to obtain the proper pure p20 polypeptide. It was found that the concentration of the sodium chloride is quite critical for obtaining the optimal polypeptide fraction being in the range of 0.15M to 5M, and preferably between 0.35M to 2.0M. Using concentrations of sodium chloride below 0.15M a very small quantity of polypeptide is obtained. Additional p20 polypeptide could be obtained from the sucrose gradient fractions by a second extraction with a sodium chloride solution. In this case the extract will be contaminated with undesirable constituents. Although in the present specification the use of sodium chloride was illustrated as extractant, one may be able to use other alkali chlorides such as potassium chloride or a mixture of sodium chloride and potassium chloride.

In the following Table 1, the amino acid compositions of the p20 polypeptide, produced according to the present invention, is shown.

TABLE 1

Amino acid analysis (mole %) of p20 polypeptide and similar proteins previously described

|  | p20[a] | Band I[b] | HMGa[c] | HM[d] | 20 kd[e] |
|---|---|---|---|---|---|
| Aspartic acid | 11.2 | 10.0 | 8.5 | 9.4 | 10.8 |
| Threonine | 5.4 | 2.9 | 8.4 | 3.8 | 4.4 |
| Serine | 8.4 | 7.1 | 7.5 | 8.3 | 9.6 |
| Glutamic acid | 13.9 | 15.5 | 15.6 | 12.4 | 16.2 |
| Proline | 4.8 | 5.9 | 5.9 | 4.0 | 5.3 |
| Glycine | 12.4 | 7.7 | 3.6 | 13.3 | 7.7 |
| Alanine | 7.9 | 7.4 | 8.8 | 7.5 | 6.8 |
| Valine | 3.2 | 3.2 | 2.3 | 3.4 | 3.2 |
| ½ Cysteine | trace | trace | — | 1.7 | — |
| Methionine | 1.0 | <1 | — | 0.8 | trace |
| Isoleucine | 4.6 | 5.0 | 6.5 | 4.6 | 5.0 |
| Leucine | 6.7 | 7.3 | 7.5 | 7.4 | 5.9 |
| Tyrosine | 2.1 | 4.2 | 4.4 | 4.0 | 3.9 |
| Phenylalanine | 2.7 | 3.0 | 2.8 | 4.0 | 2.8 |
| Lysine | 9.8 | 14.7 | 15.9 | 11.8 | 11.7 |
| Histidine | 2.5 | 1.3 | 1.3 | 1.8 | 1.9 |
| Arginine | 3.7 | 4.7 | 5.5 | 5.1 | 4.9 |
| Lysine/arginine | 2.65 | 3.1 | 2.89 | 2.31 | 2.38 |
| aspartic acid + glutamic acid | 25.1 | 25.5 | 24.1 | 21.8 | 27.0 |

TABLE 1-continued

Amino acid analysis (mole %) of p20 polypeptide and similar proteins previously described

|  | p20[a] | Band I[b] | HMGa[c] | HM[d] | 20 kd[e] |
|---|---|---|---|---|---|
| Lysine + arginine | 13.5 | 19.4 | 21.4 | 16.9 | 16.6 |

[a]Present invention
[b]Sommer (1978)
[c]Weber & Isenberg (1980)
[d]Caron et al. (1979)
[e]Certa et al. (1984)

Similar proteins mentioned in the references given in the preamble of the specification are mentioned for comparison. As appears from the above Table I, the amino acid compositions are roughly the same, but there are some slight changes particularly in the contents of aspartic acid, threonine, serine and glycine. As mentioned in the specification the following legends to FIGS. 1, 2, and 3 are given:

FIG. 1: NaDodSO$_4$-polyacrylamide gel electrophoresis of p20 polypeptide. 7.5 µl samples of salt extracted p20 polypeptide from sucrose gradient fraction No. 2 were electrophoresed on 15% polyacrylamide gel in the presence of NaDodSO$_4$. [A] Coomassie stained, [B] Silver stained. M-standards were phosphorylase b (96 kd), bovine serum albumin (68 kd), actin (45 kd), carbonic anhydrase (29 kd), troponin C (18 kd), parvalbumin (10.5 kd). M'-molecular weight standards: bovine serum albumin (68 kd), ovalbumin (43 kd), carbonic anhydrase (29 kd), chymotrypsinogen (25 kd), lysosyme (14 kd), ribonuclease (12.6 kd). Lane I: isolated p20 polypeptide. Lane H: yeast histones acid extracted according to the procedure of Sommer.

Figure 2:
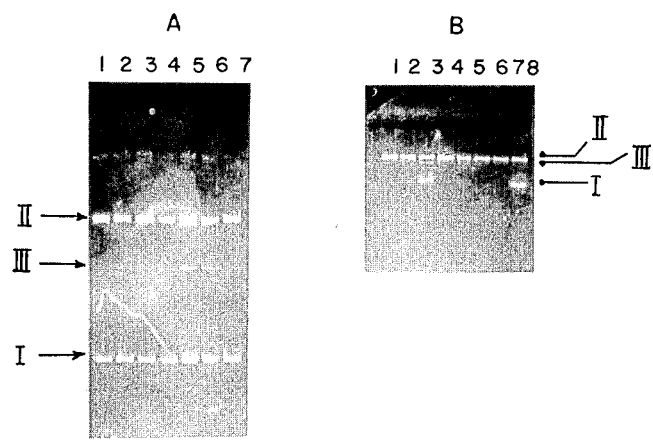
Figure 3:
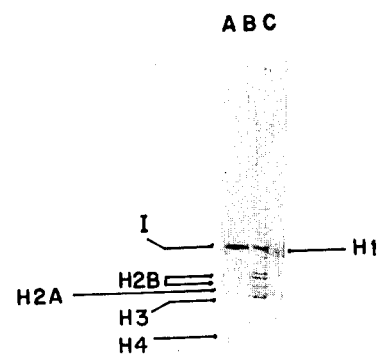

FIG. 2: Specificity of p20-DNA interactions. Purified p20 polypeptide was incubated with supercoiled [A], or relaxed [B], DNA templates in the presence or absence of GTP or ATP. [A] Lane 1, non-treated pMB9 DNA. 0.5 µg pMB9 DNA incubated at 37° C. with increasing concentrations of p20 polypeptide (0.5-1.5 µg) in the absence of 1mM GTP (Lanes 2-4), and in the presence of 1 mM GTP (Lanes 5-7). [B] Lanes 1-7, 0.5 µg enzymatically relaxed DNA incubated at 37° C. with topoisomerase I (from calf thymus, BRL) for 60 min. Lanes 2 and 3, 0.5 µg of relaxed pMB9 DNA was incubated with 0.5 µg of p20 polypeptide for 60 min at 37° C. in the absence of 1 mM GTP (Lane 2) or in the presence of 1 mM GTP (Lane 3). Lane 4, 0.5 µg of relaxed pMB9 DNA was incubated with 0.5 µg of p20 polypeptide for 60 min at 37° C. in the presence of 1 mM ATP (Lane 6), or 1 mM UTP (Lane 7). Non-treated pMB9 DNA (Lane 8).

FIG. 3: Acid-urea polyacrylamide gel electrophoresis. 5 µl samples of salt extracted p20 polypeptide from sucrose gradient fraction No. 2 were electrophoresed on 15% polyacrylamide acid-urea microslab gel (90×70×0.8 mm). Electrophoresis was carried out at 220 V for 2 h at 4° C. Lane A: 5 µg isolated band I protein. Lane B: Yeast histones prepared by the procedure of Sommer. Lane C: 5 µg Calf thymus histones (Boehringer). The gel was Coomassie stained.

According to another embodiment of the present invention, it was found that the polypeptide can produce antibodies which are very specific in their binding properties towards mammalian ras gene products. The antibodies could be used for immunodetection on Western blots, immunofluorescene and immunoprecipitation. It was found that in order to obtain specific antibodies, the polypeptides used for immunization of animals may be in a range of 16,000 to 21,000 molecular weight.

(When Schizosaccharomyces pombe was used for the preparation of the polypeptide, the molecular weight was in the range of 29,000 to 31,000 daltons). The polypeptides obtained from Saccharomyces cerevisiae have as main characteristics concerning amino acid composition the following: aspartic+glutamic acids in the range of 21.8-27.0 mole %; lysine+arginine in the range of 13.5-21.4 mole% and a ratio of lysine to arginine in the range of 2.31-3.1.

To date, three active human ras genes have been identified: ras[H] in human bladder carcinoma cells, ras[K] in human lung and colon carcinoma cells, and ras[N] in a human neuroblastoma cell line. All members of the ras gene family encode closely related proteins approximately 21,000 daltons which have been designated p21. The level of p21 expression is similar in many different human tumor cell lines, independent of whether the cell line contains an activated ras gene detectable by transfection (Der and Cooper, 1983, Cell 32, 201–208).

Human cellular Kirsten ras 1 and ras 2 genes were localized to chromosomes 6 and 12, respectively, Human cellular Harvey ras 1 and ras 2 genes were localized to chromosomes 11 and X, respectively, Human N-ras gene was localized on chromosome No. 1 (Sakaguchi et al., 1984, Mol. and Cell Biol., 4, 989–993). The relationship of c-Ki-ras and c-Ha-ras to chromosomes 3 and 12 have been observed in human cancers (Mitelman and Levan. 1981; Hereditas 95: 79–139, Gahrton et al., 1982, Nature 297, 513–514). Thus, karyotypic aberrations do not ascertain as yet the malignancy of the cells. Human neoplasia could be determined by histological examination or by a DNA-mediated transfection assay with mouse NIH 3T3 fibroblasts. Foci of transformed cells are scored after 21 days and only 10% of the urinary tract tumors yielded foci in this test (Fujita et al., 1984, Nature 309, 464–466).

Nucleotide sequence analysis of the ras[H] transforming gene of human bladder carcinoma cells indicated that the transforming activity of this gene is a consequence of a point mutation altering amino acid 12 of p21 from glycine to valine (Tabine et al. 1982, Nature 300. 143–149; Reddy et al., 1982, Nature 300, 149–152; Capon et al., 1983, Nature 302, 33–37; Reddy, 1983, Science 220, 1061–1063.

The altered p21 protein displayed abnormal electrophoretic mobility on SDS-polyacrylamide gels. Furthermore, proteins encoded by ras[K] genes activated in four human lung and colon carcinoma cells lines, also displayed abnormal electrophoretic mobilities (Der and Cooper, 1983, Cell 32, 201–208). It further appeared that different mutations could activate the same ras[K] gene in different individual neoplasms (Der and Cooper, 1983, Cell 32, 201–208). The ras[H] gene activated in another lung carcinoma cell line encodes the normal amino acid at position 12, but is mutated at codon 61 to encode leucine rather than glutamine (Yuasa et al., 1983, Nature 303, 775–779). A ras[N] gene activated in a human neuroblastoma cell line is also mutated at codon 61 but encodes lysine rather than glutamine (Taparowsky et al., 1983, Cell 34, 581–586). Taken together, these results indicate that ras genes in human neoplasms are commonly activated by structural mutations. These mutations appear thus far to occur at codon 12 or 61, with different amino acid substitutions resulting in ras gene activation in different tumors.

An alteration at position 12 in human Ha-ras leads to loss of a restriction site for HpaII-MSpI digestion, thus providing a means of molecular diagnosis of lesions in this position (Feinberg et al. 1983, Science 220, 1175–1177). An alteration at position 61 eliminates a BstNI recognition site. Detection of human cancer cells by molecular diagnosis of restriction sites is tiresome. An easy way of diagnosis is by electrophoretic separation of proteins derived from cancer cell extracts on SDS-polyacrylamide gels, (Western blots) and staining by specific antibodies. Carcinoma cells which express ras proteins with identical electrophoretic mobility to those of normal human cells, might express the protein at a level 3–5 fold higher than primary fibroblasts or epithelial cultures (Der and Cooper, 1983, Cell 32, 201–208).

In order to obtain the anti-p20 antibodies, rabbits were immunized with 40 μg portions of salt extracted p20 polypeptide emulsified in complete Freund's adjuvant (Difco), supplemented with 5 mg Mycobacterium tuberculosis cells, and injected intradermally at multiple sites. The rabbits were given booster injections with 40 μg protein at 5 weeks after the first injection and bled 1-2 weeks later.

Figure 5A:
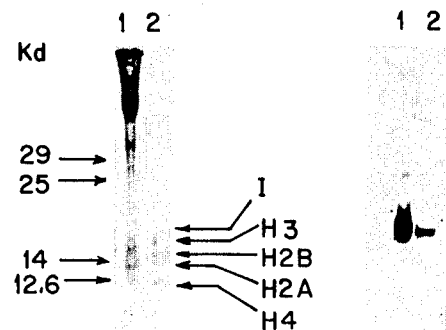

To establish the specificity of rabbit anti-p20 antibodies, immunological staining of proteins isolated from yeast chromatin by sucrose gradients and by SDS-polyacrylamide gel electrophoresis (Western blots) was performed, as illustrated in FIG. 5A. The p20 specifically reacted with the polyclonal anti-p20 antibodies. No reaction was obtained when non-immune antisera was used. FIG. 5A left—demonstrates the sucrose gradient fraction No. 2 collected from the top of the gradient (lane 1), and yeast histones prepared according to the procedure of Sommer (Lane 2), (Coomassie stained). The molecular sizes are given in daltons $\times 10^3$. Right—Electrophoretic transfer immunoblot of identical lanes as in the Coomassie stained gel, showing immunoreaction of p20 polypeptides. After incubation with antibody, the nitrocellulose paper was incubated with horseradish peroxidase protein A conjugate (Sigma). The nitrocellulose paper was washed and subsequent color development was done with hydrogen peroxide and 3,4,3',4' tetraaminobiphenyl hydrochloride.

Figure 5B:
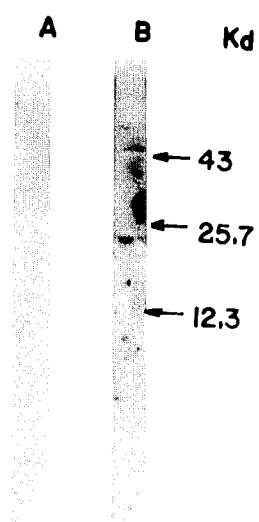

Specific determination of mammalian p21 ras proteins by anti p20 antibodies is demonstrated in FIG. 5B: Fifty μg of 3T3 NIH mouse cells transformed by Ha-murine sarcoma virus and lysed by a buffer containing 1% Triton X-100, 0.15M NaCl, 50 mM Tris-HCl (pH=7.4), 1% trasylol, 1% Na deoxycholate and 0.1% SDS were analyzed by electrophoresis in SDS-polyacrylamide gels. Western blots were incubated with non-immune serum: lane A, and with anti p20 antibody: lane B. After incubation with antibody the nitrocellulose paper was incubated with $^{125}$I-labeled protein A. The nitrocellulose paper was washed and exposed to XAR-5 film for 48 h.

The p20 prepared according to the present invention could introduce superhelical turns in relaxed pMB9 DNA as shown in FIG. 2. However, using the isolation procedure described by Certa et al. including the HPLC method with acetonitrile, the polypeptide thus obtained could not introduce superhelical turns in relaxed pMB9 DNA. This is in contrast to FIG. 2B, lane 3 which illustrates the present invention.

While the invention describing the preparation of yeast chromatin and its use for obtaining antibodies which are specific in their binding properties towards mammalian ras gene products has been illustrated with some specific embodiments, it will be understood that it is capable of further modifications and this application is intended to cover any variation, uses or adaptations of the invention and including such departures from the present disclosure as come within known or customary practice in the art to which the invention pertains and as may be applied to the essential features hereinbefore set forth and as fall within the scope of the invention. In order to further illustrate the nature of this invention for preparing the yeast chromatin and the manner for practising it, the following Example is presented for clearness of understanding only and no limitation should be understood therefrom:

Isolation of yeast chromatin: An amount of 15 g of commercial baker's yeast was washed three times with 100 ml of a buffer A solution consisting of: 24 mM Tris-HCl (pH=7.5), 10 mM MgSO$_4$, 0.4 mM EDTA and 40 mM NaHSO$_3$). The slurry was resuspended in a final volume of 36 ml of buffer A containing also 1 mM of phenyl methylsulfonyl fluoride at 0.4 g/ml. Cells were broken by shaking eight times for 1 minute at 4° C. with an equal volume of glass beads (0.5 mm, pretreated with 0.01N HCl for 60 minutes, rinsed with water until neutral, dried and coated with Sigmacote). The decanted supernatant solution was pooled, 1 mM of phenylmethylsulfonyl fluoride was added and the mixture spun for 20 minutes at 10,000 rpm at 4° C. The viscous top layer of the pellet was resuspended in 10 ml buffer A plus 1 mM phenylmethylsulfonyl fluoride and spun again. The chromatin pellet was resuspended in 20 ml of cold buffer A containing 0.3M sucrose, 0.5% NP40 (as surfactant), 1 mM phenylmethylsulfonyl fluoride and 10 mM 2-mercaptoethanol. The mixture was spun for 15 minutes at 13,000 rpm at a temperature of 4° C. The resulting pellet was dispersed in the same buffer and futher purified by centrifugation through a solution of 1.5M sucrose in buffer A containing 1 mM phenylmethylsulfonyl chloride and 10 mM 2-mercaptoethanol. The sucrose purified chromatin pellet was washed once in buffer A plus 1 mM phenylmethylsulfonyl fluoride and 10 mM 2-mercaptoethanol. The mixture was spun again for 15 minutes at 13,000 rpm at 4° C.

The washed sucrose purified chromatin pellet was washed twice in 10 mM Tris (pH=7.5), in the presence of 1 mM phenylmethylsulfonyl fluoride. Finally, the pellet was resuspended in 1.2 ml digestion buffer containing 10 mM Tris (pH=7.5), 1 mM CaCl$_2$, 0.1 mM phenylmethylsulfonyl fluoride. An amount of 30 μg micrococcal nuclease (500 U, Worthington) was added to the mixture and incubated for 10 minutes at 37° C. in an Eppendorf tube with gentle shaking. The reaction was stopped by the addition of 120 μl of 0.1M EDTA at pH=7.5 and cooled on ice. The suspension was centrifuged for 15 minutes at 12,000 rpm (at 4° C.). An amount of 0.2 ml of the clear supernatant solution plus 2 mM of phenylmethylsulfonyl fluoride was loaded per linear sucrose gradient 5–20% in 10 mM Tris-HCl (pH=7.5), 1 mM EDTA, 1 mM phenylmethylsulfonyl fluoride, 1 mM sodium bisulfite and 10 mM 2-mercaptoethanol performed in coated pollyalomar tubes. Gradients were run for 18 hours at 30,000 rpm (at 4° C.) in SW41 rotor (153,000 g). One ml fractions were collected from the top using a sterile syringe. The fractions were dialyzed overnight versus 0.1M acetic acid, lyophilized and analyzed on SDS-polyacrylamide gels.

Lyophilized sucrose gradient fractions containing the p20 polypeptide were resuspended in 50 μl of a buffer containing a solution comprising: 0.35M NaCl, 10 mM Tris-HCl, pH 8.0, 1 mM EDTA and two protease inhibitors: 1 mM phenylmethylsulfonyl fluoride and 1 mM sodium bisulfite. After 30 minutes on ice the mixture was spun at 12,000 rpm for 10 minutes. An amount of 25 μg of p20 polypeptide was obtained, based on the amino acid analysis.

I claim:

1. A method for the preparation of pure yeast chromatin for isolation of p20 peptide, which comprises the steps of:
    (a) breaking yeast cells in a solution of a buffer comprising phenylmethylsulfonyl fluoride, and centrifugation of the resultant slurry whereby a pellet of chromatin is precipitated;
    (b) purifying the precipitated pellet of chromatin by centrifugation through a sucrose solution buffered with 2-mercaptoethanol and phenylmethylsulfonyl fluoride and then washing with a buffer comprising 2-mercaptoethanol and phenylmethylsulfonyl fluoride;
    (c) solubilizing the resultant precipitate from step (b) by enzymatic digestion using a nuclease enzyme capable of digesting said precipitate;
    (d) loading the supernatant solution from the solubilized mass of step (c) on a linear sucrose gradient of 5-30% in a buffer solution containing 2-mercaptoethanol and phenylmethylsulfonyl fluoride, and
    (e) extracting the p20 polypeptide from the sucrose gradient fraction by a buffered solution comprising sodium chloride at a concentration in the range of 0.15-5M, and sodium bisulfite and phenylmethylsulfonyl fluoride at protease inhibiting concentrations.

2. A method according to claim 1, wherein the yeast includes any strain of Saccharomyces, Schizosaccharomyces; partially broken cells, isolated nuclei or mitochondria thereof.

3. A method according to claim 1, wherein the cells are broken in the presence of glass beads.

4. A method according to claim 3, wherein said glass beads are coated with Sigmacote.

5. A method according to claim 1, wherein in step (b) the concentration of sucrose is in the range of between 0.3M to 1.7M.

6. A method according to claim 1, wherein in step (b) the concentration of sucrose is in the range of 1.4M to 1.6M.

7. A method according to claim 1, wherein, in step (b) two centrifugation stages through sucrose are applied prior to said washing to improve the purification of chromatin.

8. A method according to claim 7, wherein the second centrifugation step is performed at a higher % than the first one.

9. A method according to claim 1, wherein the enzymatic digestion is carried out by a nuclease selected from the group consisting of DNase I and micrococcal nuclease.

10. A method according to claim 1, wherein the buffered solution used for the extraction of p20 polypeptide in step (e) has a sodium chloride concentration in the range of between 0.35M to 2.0M.

11. A method according to claim 1, wherein, in step (e) the extraction solution also comprises Tris-HCl, EDTA and DTE.

12. A method according to claim 2, wherein the cells are broken in the presence of glass beads.

13. A method according to claim 12, wherein said glass beads are coated with Sigmacote.

14. A method according to claim 1 wherein said enzyme used in step (c) is a deoxyribonuclease enzyme.

* * * * *